United States Patent
Tod

(10) Patent No.: US 12,023,416 B2
(45) Date of Patent: Jul. 2, 2024

(54) COLLAGEN FIBERS AND ARTICLES FORMED THEREFROM

(71) Applicant: Edwards Lifesciences Corporation, Irvine, CA (US)

(72) Inventor: Tara J. Tod, Tustin, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 858 days.

(21) Appl. No.: 16/695,042

(22) Filed: Nov. 25, 2019

(65) Prior Publication Data

US 2020/0171205 A1 Jun. 4, 2020

Related U.S. Application Data

(63) Continuation of application No. PCT/US2018/033703, filed on May 21, 2018.

(60) Provisional application No. 62/513,169, filed on May 31, 2017.

(51) Int. Cl.
| | | |
|---|---|---|
| A61L 27/24 | (2006.01) | |
| A61L 17/08 | (2006.01) | |
| A61L 27/36 | (2006.01) | |
| A61L 27/50 | (2006.01) | |
| A61L 27/58 | (2006.01) | |

(52) U.S. Cl.
CPC ........... *A61L 27/3691* (2013.01); *A61L 17/08* (2013.01); *A61L 27/24* (2013.01); *A61L 27/3683* (2013.01); *A61L 27/3687* (2013.01); *A61L 27/507* (2013.01); *A61L 27/58* (2013.01); *A61L 2430/20* (2013.01)

(58) Field of Classification Search
CPC ...... A61L 27/3691; A61L 17/08; A61L 27/24; A61L 27/3683; A61L 27/3687; A61L 27/58; A61L 2430/20
See application file for complete search history.

(56) References Cited

U.S. PATENT DOCUMENTS

| | | | |
|---|---|---|---|
| 2,393,580 | A | 1/1946 | Weiskopf |
| 4,120,649 | A | 10/1978 | Schechter |
| 4,323,358 | A | 4/1982 | Lentz et al. |
| 4,350,492 | A | 9/1982 | Wright et al. |
| 4,372,743 | A | 2/1983 | Lane |
| 4,378,224 | A | 3/1983 | Nimni et al. |
| 4,402,697 | A | 9/1983 | Pollock et al. |
| 4,405,327 | A | 9/1983 | Pollock |
| 4,481,009 | A | 11/1984 | Nashef |
| 4,553,974 | A | 11/1985 | Dewanjee |
| 4,624,822 | A | 11/1986 | Arru et al. |
| 4,647,283 | A | 3/1987 | Carpentier et al. |
| 4,648,881 | A | 3/1987 | Carpentier et al. |
| 4,758,151 | A | 7/1988 | Arru et al. |
| 4,770,665 | A | 9/1988 | Nashef |
| 4,776,853 | A | 10/1988 | Klement et al. |
| 4,786,287 | A | 11/1988 | Nashef et al. |
| 4,838,888 | A | 6/1989 | Nashef |
| 4,865,871 | A | 9/1989 | Livesey et al. |
| 4,885,005 | A | 12/1989 | Nashef et al. |
| 4,958,008 | A | 9/1990 | Petite et al. |
| 4,976,733 | A | 12/1990 | Girardot |
| 5,002,566 | A | 3/1991 | Carpentier et al. |
| 5,051,401 | A | 9/1991 | Sikes |
| 5,080,670 | A | 1/1992 | Imamura et al. |
| 5,094,661 | A | 3/1992 | Levy et al. |
| 5,104,405 | A | 4/1992 | Nimni |
| 5,116,564 | A | 5/1992 | Jansen et al. |
| 5,147,514 | A | 9/1992 | Mechanic |
| 5,154,007 | A | 10/1992 | Plunno et al. |
| 5,200,399 | A | 4/1993 | Wettlaufer et al. |
| 5,215,541 | A | 6/1993 | Nashef et al. |
| 5,279,612 | A | 1/1994 | Eberhardt |
| 5,329,846 | A | 7/1994 | Bonutti |
| 5,397,353 | A | 3/1995 | Oliver et al. |
| 5,437,287 | A | 8/1995 | Phillips et al. |
| 5,447,536 | A | 9/1995 | Girardot et al. |
| 5,460,962 | A | 10/1995 | Kemp |
| 5,476,516 | A | 12/1995 | Seifter et al. |
| 5,509,932 | A | 4/1996 | Keogh et al. |
| 5,558,875 | A | 9/1996 | Wang |
| 5,595,571 | A | 1/1997 | Jaffe et al. |
| 5,613,982 | A | 3/1997 | Goldstein |

(Continued)

FOREIGN PATENT DOCUMENTS

| | | |
|---|---|---|
| EP | 0169259 A1 | 1/1986 |
| EP | 2394673 A1 | 12/2011 |

(Continued)

OTHER PUBLICATIONS

Sigma-Aldrich. Hanks' Balanced Salts [HBSS]. Sigma-Aldrich. 2007;1.*
De Castro Bras et al. Texas 3-Step decellularization protocol: Looking at the cardiac extracellular matrix. J Proteomics. 2013;86:43-52.*
Carpentier, A., et al., "Biological Factors Affecting Long-Term Results of Valvular Heterografts," Forty-ninth Meeting of the American Association for Thoracic Surgery, San Francisco, CA, Mar. 31-Apr. 2, 1969.
Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.

(Continued)

*Primary Examiner* — Lynn Y Fan
(74) *Attorney, Agent, or Firm* — Darren M. Franklin; Nathan Lee; Sheppard, Mullin, Richter & Hampton LLP

(57) ABSTRACT

Methods of manufacturing collagen fibers comprising any one, a combination or all of the following: at least partially decellularizing a collagenous tissue; homogenizing the collagenous tissue; separating at least a portion of collagen fibers from the collagenous tissue; exposing the collagen fibers to an acidic solution before or after the separating; and forming at least one of a suture, a woven structure, a knitted structure, or a bioprosthetic device with the collagen fibers.

14 Claims, No Drawings

(56) References Cited

U.S. PATENT DOCUMENTS

| | | |
|---|---|---|
| 5,645,587 A | 7/1997 | Chanda et al. |
| 5,674,298 A | 10/1997 | Levy et al. |
| 5,697,972 A | 12/1997 | Kim et al. |
| 5,713,953 A | 2/1998 | Vallana et al. |
| 5,720,777 A | 2/1998 | Jaffe et al. |
| 5,720,894 A | 2/1998 | Neev et al. |
| 5,733,339 A | 3/1998 | Girardot et al. |
| 5,746,775 A | 5/1998 | Levy et al. |
| 5,766,520 A | 6/1998 | Bronshtein |
| 5,769,780 A | 6/1998 | Hata et al. |
| 5,782,914 A | 7/1998 | Schankereli |
| 5,782,931 A | 7/1998 | Yang et al. |
| 5,843,180 A | 12/1998 | Jaffe et al. |
| 5,843,181 A | 12/1998 | Jaffe et al. |
| 5,855,620 A | 1/1999 | Bishopric et al. |
| 5,862,806 A | 1/1999 | Cheung |
| 5,873,812 A | 2/1999 | Ciana et al. |
| 5,899,936 A | 5/1999 | Goldstein |
| 5,911,951 A | 6/1999 | Girardot et al. |
| 5,919,472 A | 7/1999 | Trescony et al. |
| 5,921,980 A | 7/1999 | Kim |
| 5,931,969 A | 8/1999 | Carpentier et al. |
| 5,935,168 A | 8/1999 | Yang et al. |
| 5,945,319 A | 8/1999 | Keogh |
| 5,977,153 A | 11/1999 | Camiener |
| 5,993,844 A | 11/1999 | Abraham et al. |
| 6,008,292 A | 12/1999 | Lee et al. |
| 6,017,741 A | 1/2000 | Keogh |
| 6,093,530 A | 7/2000 | McIlroy et al. |
| 6,106,555 A | 8/2000 | Yang |
| 6,117,979 A | 9/2000 | Hendriks et al. |
| 6,121,041 A | 9/2000 | Mirsch, II et al. |
| 6,132,472 A | 10/2000 | Bonutti |
| 6,132,473 A | 10/2000 | Williams et al. |
| 6,132,986 A | 10/2000 | Pathak et al. |
| 6,156,030 A | 12/2000 | Neev |
| 6,156,531 A | 12/2000 | Pathak et al. |
| 6,165,215 A | 12/2000 | Rottenberg et al. |
| 6,166,184 A | 12/2000 | Hendriks et al. |
| 6,174,331 B1 | 1/2001 | Moe et al. |
| 6,177,514 B1 | 1/2001 | Pathak et al. |
| 6,190,407 B1 | 2/2001 | Ogle et al. |
| 6,193,749 B1 | 2/2001 | Schroeder et al. |
| 6,203,755 B1 | 3/2001 | Odland |
| 6,206,917 B1 | 3/2001 | Williams et al. |
| 6,210,957 B1 | 4/2001 | Carpentier et al. |
| 6,214,054 B1 | 4/2001 | Cunanan et al. |
| 6,214,055 B1 | 4/2001 | Simionescu et al. |
| 6,231,608 B1 | 5/2001 | Stone |
| 6,231,614 B1 | 5/2001 | Yang |
| 6,251,579 B1 | 6/2001 | Moore et al. |
| 6,254,635 B1 | 7/2001 | Schroeder et al. |
| 6,267,786 B1 | 7/2001 | Stone |
| 6,277,555 B1 | 8/2001 | Duran et al. |
| 6,287,338 B1 | 9/2001 | Sarnowski et al. |
| 6,293,970 B1 | 9/2001 | Wolfinbarger, Jr. et al. |
| 6,302,909 B1 | 10/2001 | Ogle et al. |
| 6,312,474 B1 | 11/2001 | Francis et al. |
| 6,322,593 B1 | 11/2001 | Pathak et al. |
| 6,328,762 B1 | 12/2001 | Anderson et al. |
| 6,334,873 B1 | 1/2002 | Lane et al. |
| 6,352,708 B1 | 3/2002 | Duran et al. |
| 6,364,905 B1 | 4/2002 | Simpson et al. |
| 6,375,680 B1 | 4/2002 | Carlyle |
| 6,383,732 B1 | 5/2002 | Stone |
| 6,391,538 B1 | 5/2002 | Vyavahare et al. |
| 6,394,096 B1 | 5/2002 | Constantz |
| 6,448,076 B2 | 9/2002 | Dennis et al. |
| 6,468,660 B2 | 10/2002 | Ogle et al. |
| 6,471,723 B1 | 10/2002 | Ashworth et al. |
| 6,479,079 B1 | 11/2002 | Pathak et al. |
| 6,482,199 B1 | 11/2002 | Neev |
| 6,506,339 B1 | 1/2003 | Girardot et al. |
| 6,509,145 B1 | 1/2003 | Torrianni |
| 6,534,004 B2 | 3/2003 | Chen et al. |
| 6,547,827 B2 | 4/2003 | Carpentier et al. |
| 6,561,970 B1 | 5/2003 | Carpentier et al. |
| 6,569,200 B2 | 5/2003 | Wolfinbarger, Jr. et al. |
| 6,582,464 B2 | 6/2003 | Gabbay |
| 6,589,591 B1 | 7/2003 | Mansouri et al. |
| 6,605,667 B1 | 8/2003 | Badejo et al. |
| 6,617,142 B2 | 9/2003 | Keogh et al. |
| 6,630,001 B2 | 10/2003 | Duran et al. |
| 6,652,594 B2 | 11/2003 | Francis et al. |
| 6,653,062 B1 | 11/2003 | DePablo et al. |
| 6,682,559 B2 | 1/2004 | Myers et al. |
| 6,696,074 B2 | 2/2004 | Dai et al. |
| 6,734,018 B2 | 5/2004 | Wolfinbarger, Jr. et al. |
| 6,753,181 B2 | 6/2004 | Atala |
| 6,790,229 B1 | 9/2004 | Berreklouw |
| 6,797,000 B2 | 9/2004 | Simpson et al. |
| 6,872,226 B2 | 3/2005 | Cali et al. |
| 6,878,168 B2 | 4/2005 | Carpentier et al. |
| 6,908,591 B2 | 6/2005 | MacPhee et al. |
| 6,911,043 B2 | 6/2005 | Myers et al. |
| 6,919,172 B2 | 7/2005 | DePablo et al. |
| 7,008,763 B2 | 3/2006 | Cheung |
| 7,029,434 B2 | 4/2006 | Carpentier et al. |
| 7,037,333 B2 | 5/2006 | Myers et al. |
| 7,063,726 B2 | 6/2006 | Crouch et al. |
| 7,078,163 B2 | 7/2006 | Torrianni |
| 7,141,064 B2 | 11/2006 | Scott et al. |
| 7,143,769 B2 | 12/2006 | Stoltz et al. |
| 7,214,344 B2 | 5/2007 | Carpentier et al. |
| 7,238,200 B2 | 7/2007 | Lee et al. |
| 7,318,998 B2 | 1/2008 | Goldstein et al. |
| 7,338,757 B2 | 3/2008 | Wolfinbarger, Jr. et al. |
| 7,354,749 B2 | 4/2008 | Fisher et al. |
| 7,367,969 B2 | 5/2008 | Stoltz et al. |
| RE40,570 E | 11/2008 | Carpentier et al. |
| 7,498,565 B2 | 3/2009 | Silberberg et al. |
| 7,579,381 B2 | 8/2009 | Dove |
| 7,594,974 B2 | 9/2009 | Cali et al. |
| 7,648,676 B2 | 1/2010 | Mills et al. |
| 7,682,304 B2 | 3/2010 | Heynick-Jantz et al. |
| 7,914,569 B2 | 3/2011 | Nguyen et al. |
| 7,919,112 B2 | 4/2011 | Pathak et al. |
| 7,964,704 B2 * | 6/2011 | Huang .................. C07K 14/78 |
| | | 530/356 |
| 7,972,376 B1 | 7/2011 | Dove et al. |
| 8,007,992 B2 | 8/2011 | Tian et al. |
| 8,038,708 B2 | 10/2011 | Case et al. |
| 8,043,450 B2 | 10/2011 | Cali et al. |
| 8,075,615 B2 | 12/2011 | Eberhardt et al. |
| 8,105,375 B2 | 1/2012 | Navia et al. |
| 8,136,218 B2 | 3/2012 | Millwee et al. |
| 8,308,797 B2 | 11/2012 | Paniagua et al. |
| 8,361,144 B2 | 1/2013 | Fish et al. |
| 8,377,143 B2 | 2/2013 | Hamby et al. |
| 8,475,827 B2 | 7/2013 | Hamby et al. |
| 2001/0000804 A1 | 5/2001 | Goldstein et al. |
| 2001/0025196 A1 | 9/2001 | Chinn et al. |
| 2001/0027344 A1 | 10/2001 | Bonutti |
| 2001/0032024 A1 | 10/2001 | Cunanan et al. |
| 2001/0039459 A1 | 11/2001 | Stone |
| 2002/0001834 A1 | 1/2002 | Keogh et al. |
| 2002/0091441 A1 | 7/2002 | Guzik |
| 2002/0111532 A1 | 8/2002 | Pathak et al. |
| 2003/0035843 A1 | 2/2003 | Livesey et al. |
| 2003/0125805 A1 | 7/2003 | Johnson et al. |
| 2003/0135284 A1 | 7/2003 | Crouch et al. |
| 2003/0167089 A1 | 9/2003 | Lane |
| 2003/0212454 A1 | 11/2003 | Scott et al. |
| 2004/0030381 A1 | 2/2004 | Shu |
| 2004/0086543 A1 | 5/2004 | Keogh et al. |
| 2004/0158320 A1 | 8/2004 | Simionescu et al. |
| 2005/0010773 A1 | 1/2005 | Lapstun et al. |
| 2005/0013870 A1 * | 1/2005 | Freyman ............. C12N 5/0679 |
| | | 435/325 |
| 2005/0119736 A1 | 6/2005 | Zilla et al. |
| 2005/0136510 A1 | 6/2005 | Hendriks et al. |
| 2005/0211680 A1 | 9/2005 | Li et al. |
| 2006/0084957 A1 | 4/2006 | Delfyett et al. |
| 2006/0099326 A1 | 5/2006 | Keogh et al. |

(56) References Cited

U.S. PATENT DOCUMENTS

| | | |
|---|---|---|
| 2006/0110370 A1 | 5/2006 | Pathak et al. |
| 2006/0159641 A1 | 7/2006 | Girardot et al. |
| 2006/0193885 A1 | 8/2006 | Leonard Neethling et al. |
| 2006/0210960 A1 | 9/2006 | Livesey et al. |
| 2006/0217804 A1 | 9/2006 | Dove |
| 2006/0217805 A1 | 9/2006 | Dove |
| 2007/0050014 A1 | 3/2007 | Johnson |
| 2007/0073392 A1 | 3/2007 | Heyninck-Jantz et al. |
| 2007/0203576 A1 | 8/2007 | Lee et al. |
| 2007/0254005 A1 | 11/2007 | Pathak et al. |
| 2008/0302372 A1 | 12/2008 | Davidson et al. |
| 2008/0319166 A1 | 12/2008 | Shen |
| 2009/0041729 A1 | 2/2009 | Wolfinbarger, Jr. et al. |
| 2009/0130162 A2 | 5/2009 | Pathak et al. |
| 2009/0137999 A1 | 5/2009 | Silberberg et al. |
| 2009/0188900 A1 | 7/2009 | Cali et al. |
| 2009/0326524 A1 | 12/2009 | Cali et al. |
| 2010/0036484 A1 | 2/2010 | Hariton et al. |
| 2011/0020864 A1 | 1/2011 | Huang |
| 2011/0092966 A1 | 4/2011 | Guo et al. |
| 2011/0177150 A1 | 7/2011 | Pathak et al. |
| 2011/0214398 A1 | 9/2011 | Liburd et al. |
| 2011/0238167 A1 | 9/2011 | Dove et al. |
| 2011/0295363 A1 | 12/2011 | Girard et al. |
| 2011/0300625 A1 | 12/2011 | Paniagua et al. |
| 2011/0306124 A1 | 12/2011 | Strasly et al. |
| 2011/0311493 A1 | 12/2011 | Dove et al. |
| 2012/0035720 A1 | 2/2012 | Cali et al. |
| 2012/0059487 A1 | 3/2012 | Cunanan et al. |
| 2012/0067855 A1 | 3/2012 | Guo et al. |
| 2012/0078356 A1 | 3/2012 | Fish et al. |
| 2012/0095551 A1 | 4/2012 | Navia et al. |
| 2012/0123557 A1 | 5/2012 | Carpentier et al. |
| 2012/0141417 A1* | 6/2012 | Voytik-Harbin ........ C08L 89/06 424/93.1 |
| 2012/0185038 A1 | 7/2012 | Fish et al. |
| 2012/0328905 A1 | 12/2012 | Guo et al. |
| 2013/0122583 A1 | 5/2013 | Neethling |
| 2013/0238088 A1 | 9/2013 | Navia et al. |
| 2015/0088247 A1 | 3/2015 | L'Heureux et al. |
| 2015/0367030 A1* | 12/2015 | Murray ................... A61L 27/56 435/68.1 |

FOREIGN PATENT DOCUMENTS

| | | |
|---|---|---|
| KR | 101341704 B1 | 12/2013 |
| WO | 8401894 A1 | 5/1984 |
| WO | 9511047 A1 | 4/1995 |
| WO | 9522361 A1 | 8/1995 |
| WO | 9534332 A1 | 12/1995 |
| WO | 9613227 A1 | 5/1996 |
| WO | 9807452 A1 | 2/1998 |
| WO | 9843556 A1 | 10/1998 |
| WO | 0032252 A1 | 6/2000 |
| WO | 2004082536 A1 | 9/2004 |
| WO | 2006026325 A2 | 3/2006 |
| WO | 2006099334 A2 | 9/2006 |
| WO | 2013009851 A2 | 1/2013 |

OTHER PUBLICATIONS

Chvapil, M., et al., "Use of Chemically Purified And Cross-Linked Bovine Pericardium As A Ligament Substitute," Journal of Biomedical Materials Research, vol. 21, No. 12, pp. 1383-1394, 1987, University of Arizona Health Science Center, Tucson, AZ.

Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.

Fahner, P., et al., "Systematic Review of Preservation Methods and Clinical Outcome of Infrainguinal Vascular Allografts," Journal of Vascular Surgery, vol. 44, No. 3, pp. 518-524, 2006.

Fumoto, H., et al., "Performance of Bioprosthetic Valves After Glycerol Dehydration, Ethylene Oxide Sterilization, and Rehydration," Innovations, vol. 6, No. 1, Jan./Feb. 2011.

Grabenwoger, M. et al. "Decreased Tissue Reaction to Bioprosthetic Heart Valve Material after L-glutaimc acid Treatment. A Morphological Study." J. Biomed Mater. Res. Sep. 1992;26(9):1231-40.

Grant, R.A., et al., "The Effects of Irradiation with High Energy Electrons on the Structure and Reactivity of Native and Cross-Linked Collagen Fibres," J. Cell Sci. vol. 7, 99. 387-405, 1970.

Hauschka, P., et al., "Direct Identification of the Calcium- Binding Amino Acid, γ-Carboxyglutamate, in Mineralized Tissue," Proc. Nat. Acad. Sci, vol. 72, No. 10, pp. 3925-3929, Oct. 1975.

Jayakrishnan, A., et al., "Glutaraldehyde as a Fixative in Bioprostheses and Drug Delivery Matrices," Biomaterials, vol. 17, Issue 5, 1996, pp. 471-484.

Khora, Eugene, "Methods for the Treatment of Collagenous Tissues for Bioprostheses," Biomaterials, vol. 18, Issue 2, Jan. 1997, pp. 95-105.

Liao, K., et al., "Mechanical Stress: An Independent Determinant of Early Bioprosthetic Calcification in Humans," Ann. Throac. Surg 2008;86:491-495.

Neethling, W., et al., "Enhanced Biostability and Biocompatibility of Decellularized Bovine Pericardium, Crosslinked with an Ultra-Low Concentration Monomeric Aldehyde and Treated with ADAPT®," J. Heart Valve Dis. 2008; 17:456-464.

Olde Damink, L.H.H., et al., "Influence of Ethylene Oxide Gas Treatment on the in vitro Degradation Behavior of dermal Sheep Collagen," Journal of Biomedical Materials Resarch, vol. 29, pp. 149-155, 1995.

R Parker, et al. Storage of Heart Valve Allografts in Glycerol With Subsequent Antibiotic Sterilisation, Thorax, 1978, 638-645, vol. 33:5, British Thoracic Society, London, UK.

Saegeman, V., et al., "Short and long term bacterial inhibiting effect of high concentrations of glycerol used in the prevention of skin allografts," Science Direct, Burns, No. 34, Mar. 2008.

Schmidt, C., et al., "Acellular Vascular Tissues: Natural Biomaterials for Tissue Repair and Tissue Engineering." Biomaterials, vol. 21, pp. 2215-2231, 2000.

Trantina-Yates AE, et al. "Detoxification of Top Enhanced, Diamine-Extended Glutaraldehyde Fixation Significantly Reduces Bioprosthetic Root Calcification in the Sheep Model," J. Heart Valve Dis. Jan. 2003; 12(1):93-100.

Zilla, P., et al., "Carbodiimide Treatment Dramatically Potentiates the Anticalcific Effect of Alpha-Amino Oleic Acid on Glutaraldehyde-Fixed Aortic Wall Tissue," The Annals of Thoracic Surgery, Elsevier, vol. 79, No. 3, ISSN: 0003-4975; Mar. 1, 2005.

* cited by examiner

COLLAGEN FIBERS AND ARTICLES FORMED THEREFROM

CROSS REFERENCE TO RELATED APPLICATION

This application is a continuation of International Patent Application No. PCT/US2018/033703, filed May 21, 2018, which claims the benefit of Patent Application No. 62/513,169, filed May 31, 2017, the entire disclosures which are incorporated by reference for all purposes.

TECHNICAL FIELD

This invention relates to collagenous threads and, more particularly, to articles formed from collagen threads, such as sutures, bioprosthetic tissues, and scaffolds for engineered tissues, as well as devices incorporating collagen threads.

BACKGROUND

Collagen is the most abundant protein found in the human body. Like all other proteins, collagen is comprised of amino acids that are covalently linked through peptide or amide bonds. The sequence of the amino acids, or the primary structure, outlines the three-dimensional structure of the protein which in turn dictates the function and properties of the molecule. Collagen is composed of three peptide chains associated in a triple helical orientation. These triple helices associate to form fibrils which ultimately make up connective tissue and other structural members. The unique chemistry of collagen makes it an ideal material for structural and hemostatic applications in both clinical and diagnostic settings.

Many replacement heart valves on the market today incorporate biological tissue to form the leaflet structure. Bovine and porcine pericardium are among the most common types of biological tissue used to fabricate heart valve leaflets for replacement heart valves. The problem with these materials, however, is that they must be chemically treated to preserve and/or to render the tissues non-antigenic to the human host. Such chemical treatments, however, have been demonstrated to lead to calcification of the leaflets. While there have been attempts to utilize engineered tissue leaflets, such attempts have been met with challenges in producing a tissue having sufficient strength to withstand the hemodynamic forces in a heart valve.

It would be desirable to have a material that can be used in implantable bioprosthetic implants and that can have the tunability to design the mechanical and physical characteristics necessary for the implant.

SUMMARY

In one embodiment, a method of manufacturing collagen fibers is provided. The method can comprise any one, a combination, or all of the following: at least partially decellularizing a collagenous tissue; homogenizing the collagenous tissue; separating at least a portion of collagen fibers from the collagenous tissue; exposing the collagen fibers to an acidic solution before or after the separating; and forming at least one of a suture, a woven structure, a knitted structure, or a bioprosthetic device with the collagen fibers.

In an optional aspect, the method can further comprise lyophilizing the collagenous tissue before the at least partially decellularizing. The at least partially decellularizing can be performed by sonication. The at least partially decellularizing can also be performed by suspending the collagenous tissue in a detergent solution. The detergent solution can comprise a lysis buffer.

In another optional aspect, the method can further comprise incubating the collagenous tissue, at a temperature of at least about 4° C. for a period of time, after the homogenizing. The period of time can be from about 1 hour to about 24 hours.

In another optional aspect, the separating can be performed by centrifugation. The method can further comprise discarding a supernatant solution resulting from the centrifugation.

In another optional aspect, the acidic solution of the exposing can comprise one or a combination of acetic acid, formic acid, and citric acid.

In another optional aspect, the method can further comprise exposing the collagen fibers to a salt or a salt solution after exposing the collagen fibers to the acidic solution. The salt or salt solution can comprise any one or a combination of sodium chloride, potassium chloride, sodium phosphate, potassium phosphate, and ammonium sulfate.

In another optional aspect, the method can comprise precipitating the collagen fibers after exposing the collagen fibers to the salt or the salt solution.

In another optional aspect, the collagen fibers can have a purity of about 95% or more following separating at least a portion of the collagen fibers from the collagenous tissue.

In another optional aspect, the at least partially decellularizing can be performed without enzymes or without proteolytic enzymes.

In another embodiment, a collagen fiber having about 95% or more purity is provided. The collagen fiber is produced by the methods described herein. A suture, a bioprosthetic tissue, or a heart valve leaflet can be formed from the collagen fibers.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF EXEMPLARY EMBODIMENTS

Specific, non-limiting embodiments of the present invention will now be described. It should be understood that such embodiments are by way of example only and merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

The collagen fibers manufactured in accordance with the methods described herein can be used for manufacturing sutures, tissue scaffolds, and bioprosthetic tissues for use in a wide variety of implantable medical devices such as stent grafts, heart valves, aortic conduits, vascular patches, and any other implantable medical device that can include bioprosthetic tissues. Collagen fibers are particularly advantageous for forming sutures, tissue scaffolds, and implantable devices because of their biocompatibility and also because they can afford the ability to design and tailor the fiber orientation and thickness of the suture, tissue scaffolds and bioprosthetic tissues based on the demands of the implanted in vivo environment.

Collagen Fibers.

As used herein, "collagen fibers" is understood to include collagen that is precipitated in a fibrous form (i.e., having a length and diameter) by contacting homogenized collagenous tissue with an acid solution, a salt or salt solution, or both.

The collagenous tissue described herein can be a biological tissue. In one embodiment, the biological tissue can be any connective or collagenous tissue, whether from animal or human sources. The biological tissue can also be native cardiac valves, blood vessels, skin, hides, epidermis, dura mater, pericardium, small intestinal submucosa, ligaments, tendons, tails, particularly rodent tails, hooves and feet, particularly cow or calf feet. The biological tissue can also be pericardial tissue from animal sources, including but not limited to bovine, porcine, and equine pericardium. The biological tissue can be any one or a combination of the foregoing biological tissues. In one optional embodiment, collagenous tissue excludes intestines, engineered tissues, or both.

The acid solution that can be used in the methods described herein have a pH of about 7 or less, about 6 or less, about 5 or less, about 4 or less, about 3 or less, about 2 or less or about 1 or less. The acid solution can also have a pH including and between any two of the foregoing values. The acid that is used can be any one or a combination of acetic acid, formic acid, and citric acid.

The salt or salt solution that is used to precipitate the collagen fibers can include any salt suitable for precipitating collagen fibers, for example, any one or a combination of sodium chloride, potassium chloride, potassium phosphate, sodium phosphate, ammonium sulfate. In one embodiment, the salt excludes chromium compounds, for example, chromium salts or chromic acid salts.

In embodiments where the collagenous tissue is contacted with both the acid solution and the salt or salt solution, the collagenous tissue can be contacted first with one of the acid solution and the salt or salt solution and then with the other one of the acid solution and the salt or salt solution. Alternatively, the collagenous tissue can be contacted with a solution comprising both the acid solution and the salt or salt solution.

In one optional embodiment, a length of a collagen fiber or an average length of a group of collagen fibers that is precipitated in the fibrous form can be about 1 mm or greater, about 2 mm or greater, about 3 mm or greater, about 4 mm or greater, about 5 mm or greater, about 6 mm or greater, about 7 mm or greater, about 8 mm or greater, about 9 mm or greater, about 10 mm or greater, about 15 mm or greater, about 20 mm or greater, about 25 mm or greater, about 30 mm or greater, about 35 mm or greater, about 40 mm or greater, about 45 mm or greater, about 50 mm or greater, about 55 mm or greater, about 60 mm or greater, about 65 mm or greater, about 70 mm or greater, about 75 mm or greater, about 80 mm or greater, about 85 mm or greater, about 90 mm or greater, about 95 mm or greater, about 100 mm or greater, about 105 mm or greater, about 110 mm or greater, about 115 mm or greater, about 120 mm or greater, about 125 mm or greater, about 130 mm or greater, about 135 mm or greater, about 140 mm or greater, about 145 mm or greater, about 150 mm or greater, about 155 mm or greater, about 160 mm or greater, about 165 mm or greater, about 170 mm or greater, about 175 mm or greater, about 180 mm or greater, about 185 mm or greater, about 190 mm or greater, about 195 mm or greater, and about 200 mm or greater. The length or average length of the collagen fibers can be any value between and including any two of the foregoing values.

In another optional embodiment, a diameter of a collagen fiber or an average diameter of a group of collagen fibers can be about 1,000 microns or less, about 950 microns or less, about 900 microns or less, about 850 microns or less, about 800 microns or less, about 750 microns or less, about 700 microns or less, about 650 microns or less, about 600 microns or less, about 550 microns or less, about 500 microns or less, about 450 microns or less, about 400 microns or less, about 350 microns or less, about 300 microns or less, about 250 microns or less, about 200 microns or less, about 150 microns or less, about 100 microns or less, about 95 microns or less, about 90 microns or less, 85 about microns or less, about 80 microns or less, about 75 microns or less, about 70 microns or less, about 65 microns or less, about 60 microns or less, about 55 microns or less, about 50 microns or less, about 45 microns or less, about 40 microns or less, about 35 microns or less, about 30 microns or less, about 25 microns or less, about 20 microns or less, about 15 microns or less, about 10 microns or less, about 5 microns or less, and about 1 micron or less. The diameter or the average diameter of the collagen fibers can be a value between and including any two of the foregoing values. In a further aspect of the embodiment, the collagen fibers can each have varying diameters along its length (e.g., wavy) and thus characterized as having an average diameter along its length.

Methods of Manufacturing Collagen Fibers.

In one embodiment, methods of manufacturing collagen fibers are provided. The methods can comprise any one, a combination, or all of the following steps: producing a collagen powder from a collagenous tissue, at least partially decellularizing the collagenous tissue, homogenizing the collagenous tissue, incubating the collagenous tissue, separating at least a portion of collagen fibers from the collagenous tissue, exposing the collagen fibers to an acidic solution before or after the separating, and precipitating the collagen fibers.

Producing a Collagen Powder from a Collagenous Tissue.

The collagenous tissue can be pulverized to form a collagen fiber. In one embodiment, the collagenous tissue is frozen and then pulverized into a collagen powder. In another embodiment, the collagenous tissue is dried or dehydrated and then pulverized into a collagen powder. In a further embodiment, the collagenous tissue is frozen and dried and then pulverized into a collagen fiber. There are various methods for freezing collagenous tissue that are known in the art that can be suitable such as, for example, submerging the collagenous tissue in liquid nitrogen (for example, cooled to a temperature of about −175° C. to −225° C.), exposing the collagenous tissue to dry ice, and simply placing the collagenous tissue in a freezer.

Decellularizing the Collagenous Tissue.

The collagenous tissue or collagenous powder (if the lyophilizing process is employed) can be subjected to a decellularization process. In accordance with one aspect, the decellularization can be performed before or after the collagenous tissue is lyophilized. In accordance with another aspect, the decellularization process can be performed in the absence of the lyophilizing step.

The decellularization process is intended to isolate the extracellular matrix (ECM) of the collagenous tissue from its inhabiting cells. There is a wide variety of decellularizing treatments available, such as chemical, physical, enzymatic processes, and combinations thereof. In one embodiment, decellularization can include any one or a combination of physical, chemical, and enzymatic processes. In another embodiment, the decellularization process can exclude the physical process or the enzymatic process.

In one optional embodiment, the decellularization can be performed by one or a combination of chemical processes. In accordance to an aspect of this embodiment, the collagenous tissue or powder (if lyophilized and ground) can be suspended in a lysis buffer. The lysis buffer can comprise one or more salts (e.g., NaCl, Tris-HCl, and/or EDTA), one or more surfactants, detergents, or soaps (e.g., Triton® X-100 nonionic surfactant, Dow Chemical) and/or sodium dodecyl sulfate (SDS)), or a combination of the one or more salts and detergents. The lysis buffer can comprise an ionic surfactant, such as SDS, a nonionic surfactant, such as Triton® X-100, or both. One exemplary lysis buffer comprises 100 mM NaCl, 10 mM Tris, 1 mM EDTA, 0.1% SDS and 1% Triton® X-100. The chemical process can be performed alone or in combination with additional chemical processes and/or a physical process.

In another optional embodiment, the decellularization can be performed by one or a combination of physical processes. Exemplary physical processes involve the use of temperature, force, pressure, sound disruption, and electrical disruption. In accordance with one aspect of this embodiment, a temperature method can be used. The temperature method can involve a rapid freeze-thaw mechanism. By quickly freezing a tissue, microscopic ice crystals form around the plasma membrane and the cell is lysed. In accordance with another aspect of this embodiment, direct force of pressure on the collagenous tissue or powder can be used. Pressure decellularization involves the controlled use of hydrostatic pressure applied to the collagenous tissue. In accordance with a further aspect of this embodiment, sound or electrical disruption can also be used. The decellularization results from exposing the tissue to electric pulses or soundwaves.

Homogenizing and Incubating the Collagenous Tissue.

The collagenous tissue or collagenous powder can be subjected to homogenization and incubation processes. The homogenizing process can be performed after the collagenous tissue or collagenous powder is decellularized using any suitable method and/or device, for example, mechanically, ultrasonically, under shear, and/or under pressure. Examples of a suitable homogenization devices includes rotor-stator homogenizers. In some embodiments, the tissue or powder is suspended in a liquid, for example, water, saline, or a buffer solution. In accordance with an aspect of this embodiment, the collagenous tissue or collagen powder can be homogenized at a speed of at least 5,000 rpm, at least 10,000 rpm, at least 15,000 rpm, at least 20,000 rpm, at least 25,000 rpm, or at least 30,000 rpm. Following the homogenizing process, the collagenous tissue or collagenous powder can be incubated at about 4° C. for about from 1 to 12 hours or longer.

Separating Collagen Fibers from the Collagenous Tissue.

Following the homogenizing and the incubating, the collagenous tissue or powder can be centrifuged. In accordance with an aspect of this embodiment, the collagenous tissue or powder can be provided in a suspension and centrifuged at a speed of at least about 1,000 rpm, at least about 5,000 rpm, at least about 10,000 rpm, at least about 15,000 rpm, at least about 20,000 rpm, at least about 25,000 rpm, or at least about 30,000 rpm for at least about 1 minute, at least about 5 minutes, at least about 10 minutes, at least about 15 minutes, at least about 20 minutes, at least about 25 minutes or at least about 30 minutes. The supernatant is decanted and the remaining insoluble material is washed with an acid solution, such as acetic acid.

In some embodiments, the acid solution is selected such that it does not dissolve the collagen fibers present. The acid solution that is used can have a pH of about 7 or less, about 6 or less, about 5 or less, about 4 or less, about 3 or less, about 2 or less or about 1 or less. The acid solution can also have a pH including and between any two of the foregoing values. The acid can be any one or a combination of acetic acid, formic acid, and citric acid.

In some embodiments, the acid solution causes some or all of the collagen fibers to become a gel or gel-like. The gel or gel-like material can be extruded from a spinneret into fiber. The fiber can be extruded into a salt solution and/or coextruded with a salt solution, the purpose of which is explained in greater detail below. The gel or gel-like material can also be electrospun, for example, into a fabric or coating.

The collagen fibers are then removed and exposed to a salt or a salt solution to further precipitate the collagen fibers. Exemplary salts include sodium chloride, potassium phosphate, potassium chloride, and/or ammonium sulfate.

Sutures.

Sutures can be produced from the collagen fibers described herein.

In one embodiment, a single suture can be a made from a single collagen fiber or from a plurality of collagen fibers that are braided, twisted, and/or spun together. In accordance with one aspect, the suture, whether made from a single or a plurality of collagen fibers, can be manufactured solely from collagen fibers. In accordance with another aspect, the suture can comprise one or more collagen fibers in association with a different natural or synthetic fiber or with a synthetic polymer in either monofilament or multifilament form.

In another separate embodiment, the suture can be an absorbable suture or a non-absorbable suture. The absorbable suture can break down in the tissue after a given period of time. The non-absorbable suture can be made of collagen fibers that have been chemically treated or that are provided in association with additional materials or fibers which render the suture at least partially resistant to metabolization by the body, for example, by at least partially fixing as discussed in greater detail below. In one aspect of the embodiment, the non-absorbable collagen fiber suture can be a braided suture comprising one or more collagen fibers braided together with one or more non-absorbable materials, such as silk, polypropylene, polyethylene, nylon, polyamide, polyester, polyethylene terephthalate, or metal fibers, to name a few.

Optionally, sutures comprising collagen fibers can be impregnated with a suitable coating, softening or antimicrobial agent, or colored by a color additive, for example, as approved by the U.S. Federal Drug Administration ("FDA") or other regulatory agency.

In a preferred embodiment, the suture meets the standards set forth in the United States Pharmacopeia (USP) or other standard for absorbable or non-absorbable sutures.

In a preferred embodiment, the suture is an absorbable suture or a non-absorbable suture having a knot-pull tensile strength (N) per average diameter (mm) of the suture of about 1 N/mm or more, about 2 N/mm or more, about 3 N/mm or more, about 4 N/mm or more, about 5 N/mm or more, about 10 N/mm or more, about 15 N/mm or more, about 20 N/mm or more, about 25 N/mm or more, about 30 N/mm or more, about 35 N/mm or more, about 40 N/mm or more, about 45 N/mm or more, about 50 N/mm or more, about 55 N/mm or more, about 60 N/mm or more, about 65 N/mm or more, about 70 N/mm or more, about 75 N/mm or more, about 80 N/mm or more, about 85 N/mm or more, about 90 N/mm or more, about 95 N/mm or more, about 100 N/mm or more, about 105 N/mm or more, about 110 N/mm or more, about 115 N/mm or more, about 120 N/mm or more, about 125 N/mm or more, about 130 N/mm or more, about 135 N/mm or more, about 140 N/mm or more, about 145 N/mm or more, about 150 N/mm or more, about 155 N/mm or more, about 160 N/mm or more, about 165 N/mm or more, about 170 N/mm or more, about 175 N/mm or more, about 180 N/mm or more, about 185 N/mm or more, about 190 N/mm or more, about 195 N/mm or more, about 200 N/mm or more. In another preferred embodiment, the absorbable suture has a knot-pull strength that is between any two of the foregoing values. In yet another preferred embodiment, the non-absorbable suture has a knot-pull strength that is between and includes any two of the foregoing values.

In another preferred embodiment, the suture is an absorbable or a non-absorbable suture having an elongation at break of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, and at least about 95%. In another preferred embodiment, the absorbable suture has an elongation at break that is between any two of the foregoing values. In yet another preferred embodiment, the non-absorbable suture has an elongation at break that is between and includes any two of the foregoing values.

Bioprosthetic Tissues.

The collagen fibers can be used to produce a bioprosthetic tissue by either weaving, knitting, or wrapping the collagen fibers around each other or around a substrate, or fabricating a non-woven material from the fibers. The bioprosthetic tissue that is produced using the collagen fibers can be designed to a desired dimension, thickness and porosity. The bioprosthetic tissue can then be subjected to further chemical processes to render it suitable for implantation.

In one embodiment, the collagen fibers, sutures comprising the collagen fibers, bioprosthetic tissues comprising the collagen fibers, and any medical device comprising the collagen fibers have a purity of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98% and at least about 99% of collagen proteins. In another embodiment, the collagen fibers, sutures comprising the collagen fibers, bioprosthetic tissues comprising the collagen fibers, and any medical device comprising the collagen fibers have a purity including and between any two of the foregoing values.

Further Processing of the Collagen Fibers, Sutures, or Bioprosthetic Tissues.

Fixation Process.

In one embodiment, the collagen fibers, sutures, bioprosthetic tissue or articles produced with the collagen fibers, can be subjected to a fixation or cross-linking treatment, as a result of which the collagen fibers are rendered less antigenic and are at least partially or completely cross-linked. The fixation process is understood to include any chemical, heat or other processes, as a result of which the collagen fibers are preserved and rendered mechanically and dimensionally stable. The fixation process can also be employed as part of the chemical process to render the collagen fibers resistant to being absorbed by the body or even non-absorbable.

The fixation process can include contacting the collagen fibers with one or more fixatives. Known fixatives include aldehydes, polyaldehydes, diisocyanates, carbodiimides, photo-oxidation agents, and polyepoxide compounds. In a preferred embodiment, the fixative used is glutaraldehyde. Some embodiments of glutaraldehyde-fixed tissue, however, are particularly vulnerable to calcification since glutaraldehyde fixation can generate residual aldehyde groups and labile Schiff bases. The residual aldehydes and Schiff bases can be potential binding sites for calcium. The aldehyde groups can also oxidize to carboxylic acid groups, which are known to attract and bind calcium.

Various techniques have therefore been developed to reduce the aldehyde and acid levels of glutaraldehyde-fixed tissues, and thus reduce its propensity to calcify after implantation in the patient, for example, the capping procedures described below.

The fixation process can include adjusting the pH of the glutaraldehyde fixative solution to reduce the generation of calcium binding sites, as disclosed in U.S. Pat. No. 6,878,168 to Edwards Lifesciences, the entire contents of which are incorporated herein by reference. In a preferred embodiment, the pH of the glutaraldehyde fixative solution is about or provided in a range including and between any two of the following pH values: 4.5, 5.0, 5.5, 6.0, 6.5, 7.0, 7.5, 8.0, 8.5, and 9.0.

The fixation process can also further include a heat-treating step after contacting with the one or more fixatives. Glutaraldehyde-fixed tissues have demonstrated a reduced aldehyde and carboxylic acid content after heat treatment, and thus a marked reduction in calcification after implantation, as compared to glutaraldehyde-fixed tissue without heat treatment. The glutaraldehyde fixative in solution can be heat treated before, during, or after the bioprosthetic tissue is immersed in the solution. The heat treatment can include heating the glutaraldehyde fixative in solution to a temperature of about or provided in a range including and between any two of the following temperatures: 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., and 80° C. Exemplary processes for heat treating glutaraldehyde-fixed tissue are described in U.S. Pat. No. 6,561,970, issued May 13, 2003 to Edwards Lifesciences, the entire contents of which are incorporated herein by reference. The heat treatment of glutaraldehyde-fixed tissue is commercially embodied in the Carpentier-Edwards ThermaFix® (TFX) tissue from Edwards Lifesciences.

Treatment with Capping and/or Reducing Agents.

Following or concurrently with the fixation process, the collagen fibers can be treated with a capping agent, a reducing agent, or both. The collagen fibers can include functional groups that exist either inherently in the collagen fibers, as a result of being cross-linked or fixed, or as a result of being subjected to any number of chemical or physical processes, including the pre-conditioning, pre-stressing, or pre-damaging disclosed herein. Exemplary processes for treatment with capping and/or reducing agents are described in U.S. Pat. No. 7,972,376, the entire contents of which are incorporated by reference as if fully set forth herein.

In one embodiment, the presence of these functional groups can be undesirable in certain circumstances because they can contribute to calcification of the collagen fibers when implanted in a host. For example, aldehydes, carboxylic acids, amines and other potential binding sites for calcium can interact with or attract calcium, phosphate, immunogenic factors, or other precursors to calcification. In another embodiment, the presence of the functional groups may not necessarily be undesirable, but may provide a reactive group for a further chemical reaction or for covalent bonding of an agent that is desired to be associated with the collagen fibers.

For example, negatively charged carboxylic acid groups formed after glutaraldehyde fixation of the collagen fibers may attract positively-charged calcium ions due to their negative charge, leading to calcification of the collagen fibers or other adverse cellular interactions.

Accordingly, the collagen fibers can be treated with a capping agent. The capping agent can be any agent that can block, remove or alter a functional group that can actually or potentially produce an undesirable interaction between the collagen fibers and the host, such as calcification, immunological reaction, and the like.

In one embodiment, the collagen fibers can be treated with the capping agent without the step of fixing or crosslinking the collagen fibers. In another embodiment, the collagen fibers can be treated with the capping agent before, during or after the step of fixing and/or crosslinking the collagen fibers.

As explained above, the reaction of aldehyde-containing agents, such as glutaraldehyde, and the amine groups associated with the collagen fibers can result in the formation of labile Schiff bases. It may therefore be desirable to further treat the collagen fibers to replace the Schiff bases with a more stable amine.

In one embodiment, the capping agent can include any one or a combination of the following: an amine, such as an alkyl amine, amino alcohol, and ethanolamine; an amino acid, such as lysine and hydroxylysine; an amino sulfonate, such as taurine, amino sulfates, dextran sulfate, and chondroitin sulfate; hydrophilic multifunctional polymers, such as polyvinyl alcohols and polyethyleneimines; a hydrophobic multifunctional polymer; α-dicarbonyls, including methylglyoxal, 3-deoxyglucosone, and glyoxal; hydrazines, such as adipic hydrazide; N,N-disuccinimidyl carbonate; carbodiimides, such as 1-ethyl-3-[3-dimethylaminopropyl]carbodiimide hydrochloride (EDC), N-cyclohexyl-N'-(2-morpholinoethyl)carbodiimide (CMC), and 1,3-dicyclohexyl carbodiimide (DCC); and 2-chloro-1-methylpyridinium iodide (CMPI).

In another embodiment, the capping agent can be any agent that is reactive with a functional group, wherein the functional group is a free aldehyde or a free carboxylic acid. The capping agent can be an amine, such as an alkyl amine or an amino alcohol. The capping agent can be an ethanolamine.

In a further embodiment, the capping agent can be any agent that is reactive with a functional group, wherein the functional group is an amine, a hydroxyl group, or a sulfhydryl group. In accordance with this embodiment, the capping agent can comprise a carbonyl functional group. The carbonyl functional group can be an aldehyde or a carboxylic acid and can be selected from a monoaldehyde, a polyaldehyde, a monocarboxylic acid, a polycarboxylic acid, and the like.

Regardless, certain reactions between a capping agent and a functional group can produce labile Schiff bases, and it can be desirable to reduce the Schiff bases to more stable amines.

Accordingly, the treatment of the collagen fibers can further include treatment with a reducing agent. The reducing agent can be selected to reduce at least some Schiff bases formed from the reaction of the crosslinking agent and the collagen fibers, the capping agent and the collagen fibers, and the capping agent and the crosslinking agent. In one embodiment, the collagen fibers can be treated with the reducing agent, with or without the fixing or crosslinking the collagen fibers. In another embodiment, the collagen fibers can be treated with the reducing agent, with or without the capping agent. In a further embodiment, the collagen fibers can be treated with the reducing agent, with or without both the fixing or crosslinking and capping the collagen fibers.

The reducing agent can be any one or a combination of agents that comprise a borohydride. In one embodiment, the reducing agent can be one or a combination selected from the group consisting of sodium borohydride, sodium cyanoborohydride, sodium triacetoxyborohydride, an alkyl borohydride, an amino borohydride, lithium aminoborohydrides, and an organoborate hydride salt having the formula $XBR_3H$, where R is an alkyl group and X is lithium, sodium or potassium. The lithium aminoborohydride can be a lithium dimethylaminoborohydride, a lithium morpholinoborohydride, and a lithium pyrrolidinoborohydride, to name a few. The organoborate hydride salt reducing agent can be a lithium tri-sec-butyl(hydrido)borate, a sodium tri-sec-butyl(hydrido)borate, a potassium tri-sec-butyl(hydrido)borate, or a lithium aluminum hydride. The reducing agent can also be sodium bisulfate in acetylacetone, formic acid in formaldehyde, either alone, in combination, or in combination with a borohydride reducing agent.

The collagen fibers can be subjected to a treating step in which it is contacted with a capping agent and a reducing agent in a solution. In one embodiment, the capping agent is selected to react with one or more functional groups associated with the collagen fibers and the reducing agent is selected to reduce Schiff bases. The Schiff bases can be formed from any one or more of the reaction of the crosslinking agent and the collagen fibers, the reaction of the capping agent and the collagen fibers, and the reaction of the capping agent and the crosslinking agent. The capping agent can be an amine or an amino alcohol, such as an ethanolamine, the functional group can be an aldehyde or a carboxylic acid, the reducing agent can be a borohydride, such as a sodium borohydride and the crosslinking agent can be an aldehyde-containing agent, such as a glutaraldehyde. The treating can be performed sequentially with first the capping agent and then the reducing agent in solution or simultaneously with both the capping and reducing agents present in the solution. Some embodiments include more than one capping and/or reducing step. In one embodiment, the treating can be performed with the capping agent and reducing agent in a solution on an orbital shaker operating at about 80 to about 100 rpm for about 4 hours.

Exemplary methods for treating biological tissue with capping and reducing agents are described in U.S. Pat. No. 7,972,376, issued Jul. 5, 2011, to Edwards Lifesciences Corp., the entire contents of which are incorporated by reference as if fully set forth herein.

The treatment with the capping and/or reducing agents can be performed after the fixed collagen fibers have been subjected to a process of pre-conditioning, pre-stressing, or pre-damaging to generate additional acid binding sites which can subsequently be capped, as described in U.S. Patent Publication No. 2008/0302372 A1, published Dec. 11, 2008, entitled "Methods for Pre-Stressing and Capping Bioprosthetic Tissue" to Edwards Lifesciences, the entire contents of which are incorporated herein by reference. In one embodiment, the collagen fibers can be subjected to a rapid pulsed fluid flow (in the range of from about 4 Hz to about 1,500 Hz), repeated flexion of the collagen fibers, elevated temperature (in the range of from about 26° C. to about 65° C.), an acidic solution (pH in the range of about 4 to about 7), alkaline solution (pH in the range of about 8 to about 10), or any combination of the foregoing for the purpose of generating additional acid binding sites, which may be capped and/or reduced in a separate treatment process.

Glycerol Treatment.

The collagen fibers can further undergo treatment with anhydrous, non-aqueous, or aqueous glycerol solutions to substantially, if not completely, remove interstitial water from between the collagen fibers, while retaining substantial bound water. It is believed that the glycerol at least partially replaced the interstitial water. Accordingly, the process is also referred to as "glycerolization" and the tissue referred to as "glycerolized". The collagen fibers following glycerol treatment may contain residual water or moisture within the tissue interstices, but may be suitable for packaging for dry storage, that is, without the need to be stored in a liquid. Such treatment can be applied to the fibers, textiles comprising a plurality of fibers, for example, suture or fabric, or to devices including the fibers, for example, prosthetic valves, patches, or grafts.

In one embodiment, the collagen fibers can be treated with an anhydrous, non-aqueous or aqueous solution that comprises glycerol. In one embodiment, the anhydrous, non-aqueous or aqueous solution can comprise about 25% by volume, about 30% by volume, about 35% by volume, about 40% by volume, about 45% by volume, about 50% by volume, about 55% by volume, about 60% by volume, about 65% by volume, about 70% by volume, about 75% by volume, about 80% by volume, about 85% by volume, about 90% by volume, or about 95% by volume glycerol. In another embodiment, the anhydrous, non-aqueous, or aqueous solution comprises an amount of glycerol within and including any two of the foregoing values.

In another embodiment, the anhydrous, non-aqueous, or aqueous glycerol solution can comprise at least one alcohol. In one embodiment, the anhydrous, non-aqueous, or aqueous solution can comprise about 5% by volume, about 10% by volume, about 15% by volume, about 20% by volume, about 25% by volume, about 30% by volume, about 35% by volume, 40% by volume, 45% by volume, 50% by volume, 55% by volume, 60% by volume, 65% by volume, 70% by volume, or 75% by volume alcohol. In another embodiment, the anhydrous, non-aqueous or aqueous solution comprises an amount of alcohol within and including any two of the foregoing values. The alcohol can be any one or a combination of $C_1$, $C_2$, $C_3$, $C_4$, and $C_5$ alcohols, such as ethanol, n-propanol, 2-propanol, n-butanol, 2-butanol, and isobutanol.

In one embodiment, the solution is a non-aqueous solution of about 75% by volume glycerol and 25% by volume ethanol. The collagen fibers are immersed in the solution for a period of time sufficient to permit the solution to permeate the collagen fibers. The collagen fibers are then removed from the solution to allow removal of excess solution. Suitable treatment for the biological tissues are described in U.S. Pat. No. 8,007,992, issued Aug. 30, 2011, to Edwards Lifesciences Corp., the entire contents of which are incorporated herein by reference as if fully set forth herein.

In another preferred embodiment, an aqueous glycerol solution can be used to at least partially dehydrate the collagen fibers, as described in U.S. Pat. No. 6,534,004, issued Mar. 18, 2003, to The Cleveland Clinic Foundation, the entire contents of which are incorporated herein by reference in its entirety as if fully set forth herein.

The collagen fibers can also be treated by means other than the glycerol treatment process described above to dry or dehydrate the collagen fibers. The terms "dry" or "dehydrate," as used herein with reference to the collagen fibers or the implantable bioprosthetic device, is understood to include residual water or moisture that can be present in the collagen fibers following glycerol or other treatment to reduce the water content of the collagen fibers. In one embodiment, the water content of the dried or dehydrated collagen fibers following glycerol or other treatment is about 25% by weight or less, about 20% by weight or less, about 15% by weight or less, about 10% by weight or less, about 9% by weight or less, about 8% by weight or less, about 7% by weight or less, about 6% by weight or less, about 5% by weight or less, about 4% by weight or less, about 3% by weight or less, about 2% by weight or less, or about 1% by weight or less. The percentages provided herein are understood to be based on the combined weight of the collagen fibers and water content.

Examples of other treatments suitable for drying the collagen fibers include contacting the fibers with solutions containing other polyols, for example, propylene glycol solutions. Suitable solutions and methods are similar to the solutions and methods using glycerol described above, in which the glycerol is replaced with propylene glycol, thereby replacing at least a portion of the interstitial water with propylene glycol. Other suitable methods use a polyether, for example, polyethylene glycol (PEG) or polypropylene glycol (PPG) in place of glycerol. Other embodiments use a combination of any of the above methods, simultaneously and/or sequentially. For example, interstitially water can be replaced or removed in two or more steps, contacting the collagen fibers first with a less concentrated solution, followed by contact with a more concentrated solution.

The collagen fibers can also be lyophilized or freeze-dried for dry storage. The collagen fibers can first be incubated in a cryopreservation solution that contains one or more cryoprotectants to reduce or minimize ice crystal damage to the structural matrix that could occur during freezing. Suitable cryoprotectants include polyols, diols, ethylene glycol, propylene glycol, triols, glycerol, sugars, glucose, fructose, sucrose, trehalose, sugar alcohols, mannitol, threitol, and dimethyl sulfoxide (DMSO). If the collagen fibers are to be freeze dried, the solution will generally also contain one or more dry-protective components, to minimize structural damage during drying and can include a combination of an organic solvent and water which undergoes neither expansion nor contraction during freezing. The cryoprotective and dry-protective agents can be the same one or more substances. If the collagen fibers are not going to be freeze-dried, they can be frozen by placing them (in a sterilized container) in a freezer at about −80° C., or by plunging it into sterile liquid nitrogen, and then storing at a temperature below −160° C. until use. The collagen fibers can be thawed prior to use by, for example, immersing a sterile non-permeable vessel containing a water bath at about 37° C. or by allowing the tissue to come to room temperature under ambient conditions.

Example

Bovine pericardial tissue was cut into small pieces, frozen in liquid nitrogen, and ground into a powder using a mortar and pestle. The resulting powder was suspended in a lysis buffer (100 mM NaCl, 10 mM Tris, 1 mM EDTA, 0.1% SDS, 1% Triton® X-100). The suspension is then mechanically homogenized (Cole-Parmer® LabGEN® 125 homogenizer) at full speed for several seconds.

The homogenized suspension was then incubated overnight at 4° C. Following incubation, the homogenized suspension was centrifuged at 10,000 rpm for 10 minutes to separate the collagen fibers from the supernatant, which was discarded. The remaining collagen fibers were washed with 0.25 M acetic acid, after which the collagen fibers became gel-like. A concentrated sodium chloride solution was then added to precipitate the collagen fibers. Alternatively, the concentrated salt solution can be added to the acetic acid slurry prior to separating the collagen fibers from the supernatant.

Strands of collagen fibers were removed following the precipitation, with lengths of from about 5-10 cm (about 2-4 inches), and non-uniform diameters along their lengths. A sample of the collagen fibers were twisted together to form a yarn.

It is to be understood that the detailed description and specific examples, while indicating preferred embodiments of the present disclosure, are given by way of illustration and not limitation. Many changes and modifications within the scope of the present disclosure may be made without departing from the spirit thereof, and the disclosure includes all such modifications.

What is claimed is:

1. A method of manufacturing collagen fibers, the method comprising:
   at least partially decellularizing a collagenous tissue;
   homogenizing the decellularized collagenous tissue to provide a homogenized suspension;
   incubating the homogenized suspension at a temperature of at least about 4° C. for a period of time from about 1 hour to about 24 hours;
   separating at least a portion of collagen fibers from the homogenized suspension after incubating;
   exposing the portion of collagen fibers to an acidic solution before or after the separating;
   exposing the portion of collagen fibers to a salt or a salt solution after exposing the portion of collagen fibers to the acidic solution;
   precipitating the portion of collagen fibers in a fibrous form after exposing the portion of collagen fibers to the salt or salt solution; and
   forming at least one of a suture, a woven structure, a knitted structure, or a bioprosthetic device with the precipitated collagen fibers.

2. The method of claim 1, further comprising lyophilizing the collagenous tissue before the at least partially decellularizing.

3. The method of claim 1, wherein the at least partially decellularizing is performed by sonication.

4. The method of claim 1, wherein the at least partially decellularizing is performed by suspending the collagenous tissue in a detergent solution.

5. The method of claim 4, wherein the detergent solution comprises a lysis buffer.

6. The method claim 1, wherein the separating is performed by centrifugation.

7. The method of claim 6, further comprising separating a supernatant solution resulting from the centrifugation.

8. The method of claim 1, wherein the acidic solution comprises one or a combination selected from the group consisting of: acetic acid, formic acid, and citric acid.

9. The method of claim 1, wherein the salt or salt solution comprises any one or a combination selected from the group consisting of: sodium chloride, potassium chloride, sodium phosphate, potassium phosphate, and ammonium sulfate.

10. The method claim 1, wherein the portion of collagen fibers has a purity of about 95% or greater following the separating.

11. The method claim 1, wherein the at least partially decellularizing is performed without enzymes.

12. The method claim 1, wherein the at least partially decellularizing is performed without proteolytic enzymes.

13. The method of claim 1, further comprising treating the portion of collagen fibers with a solution comprising glycerol.

14. The method of claim 1, further comprising treating the portion of collagen fibers with a solution comprising glutaraldehyde.

* * * * *